United States Patent [19]

Baudin

[11] Patent Number: 5,288,701
[45] Date of Patent: Feb. 22, 1994

[54] DERIVATIVES OF DIHYDROCAMPHOLENIC ALDEHYDE

[75] Inventor: Josianne Baudin, Annemasse, France

[73] Assignee: Givaudan-Roure Corporation, Clifton, N.J.

[21] Appl. No.: 723,996

[22] Filed: Jul. 1, 1991

[30] Foreign Application Priority Data

Jul. 12, 1990 [EP] European Pat. Off. ......... 90113324.9

[51] Int. Cl.$^5$ ............................................. A61K 7/46
[52] U.S. Cl. ...................................... 512/8; 568/838; 568/379; 568/446
[58] Field of Search .................. 568/379, 446, 838; 512/8

[56] References Cited

U.S. PATENT DOCUMENTS

| | | | |
|---|---|---|---|
| 4,052,341 | 10/1977 | Naipawer | 512/8 |
| 4,174,287 | 11/1979 | Kamath et al. | 512/8 |
| 4,208,296 | 6/1980 | Yoshida et al. | 512/8 |
| 4,501,687 | 2/1985 | Martel et al. | 512/8 |
| 4,696,766 | 9/1987 | Naipawer | 512/8 |
| 4,766,002 | 8/1988 | Rohr et al. | 568/838 |

FOREIGN PATENT DOCUMENTS

| | | | |
|---|---|---|---|
| 0093425 | 4/1983 | European Pat. Off. | 512/8 |
| 0155591 | 9/1985 | European Pat. Off. | 512/8 |
| 0203528 | 12/1986 | European Pat. Off. | 512/8 |
| 3441902 | 1/1986 | Fed. Rep. of Germany | 568/838 |

*Primary Examiner*—James H. Reamer
*Attorney, Agent, or Firm*—George M. Gould; George W. Johnston

[57] ABSTRACT

The invention concerns novel odorants, namely derivatives of dihydrocampholenic aldehyde having the formula

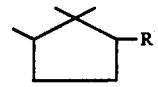

I wherein R is

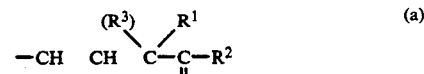
(a)

or

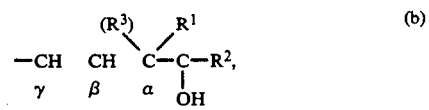
(b)

one of the dotted lines in each of (a) and (b) represents an additional bond, and, $R^1$, $R^2$ and $R^3$ are selected from the group consisting of hydrogen and alkyl groups of from one to four carbon atoms, with the proviso that $R^3$ is present only when the additional bond is between the carbon atoms designated as $\beta$ and $\gamma$.

The invention also concerns odorant compositions containing the dihydrocampholenic aldehyde derivatives and methods for making same.

6 Claims, No Drawings

DERIVATIVES OF DIHYDROCAMPHOLENIC ALDEHYDE

SUMMARY OF THE INVENTION

The invention concerns novel odorants, namely derivatives of dihydrocampholenic aldehyde having the formula

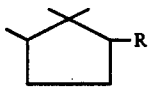

I wherein:
R is

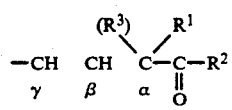   (a)

or

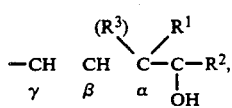   (b)

one of the dotted lines in each of (a) and (b) represents an additional bond, and, $R^1$, $R^2$ and $R^3$ are selected from the group consisting of hydrogen and alkyl groups of from one to four carbon atoms, with the proviso that $R^3$ is present only when the additional bond is between the carbon atoms designated as $\beta$ and $\gamma$.

The following subgroups comprise the ketones and alcohols of formula I:

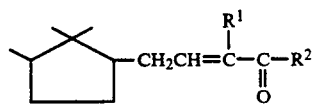 Ia

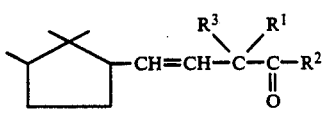 Ib

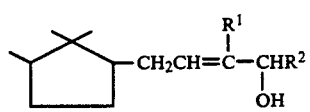 Ic

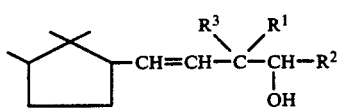 Id

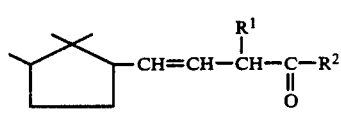 Ie

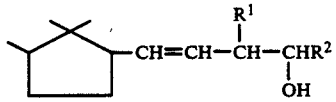 If

The (sub) generic formulas are intended to encompass all isomers, subject to asymmetric carbon atoms being present in the ring and the side chain (and thus leading to chiral centers) and a double bond being present in the side chain.

The compounds of formula I are distinguised by very natural notes in the direction of fruity and flowery. These olfactive properties make the compounds particularly valuable for use in fragrance compositions. The invention, therefore, also concerns odorant compositions containing the dihydrocampholenic aldehyde derivatives and methods for making same.

DESCRIPTION OF THE PREFERRED EMBODIMENTS

The compounds of formula I are obtained as the essential reaction products of a process comprising a) reacting dihydrocampholenic aldehyde with a compound of the formula

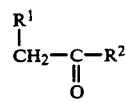

under the conditions of an aldol condensation, b) subjecting a compound of the formula

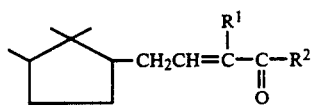 Ia to a deconjugation, and, if desired, an alkylation, c) selectively reducing the carbonyl group of a compound of the formula

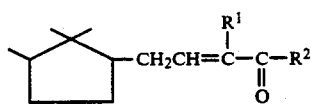 Ia or of the formula

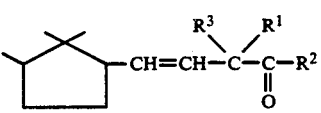 Ib or of the formula

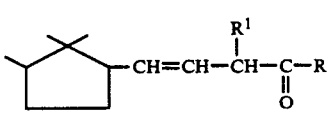 Ie

The process for the manufacture of the compounds I can be outlined as follows:

Reaction scheme

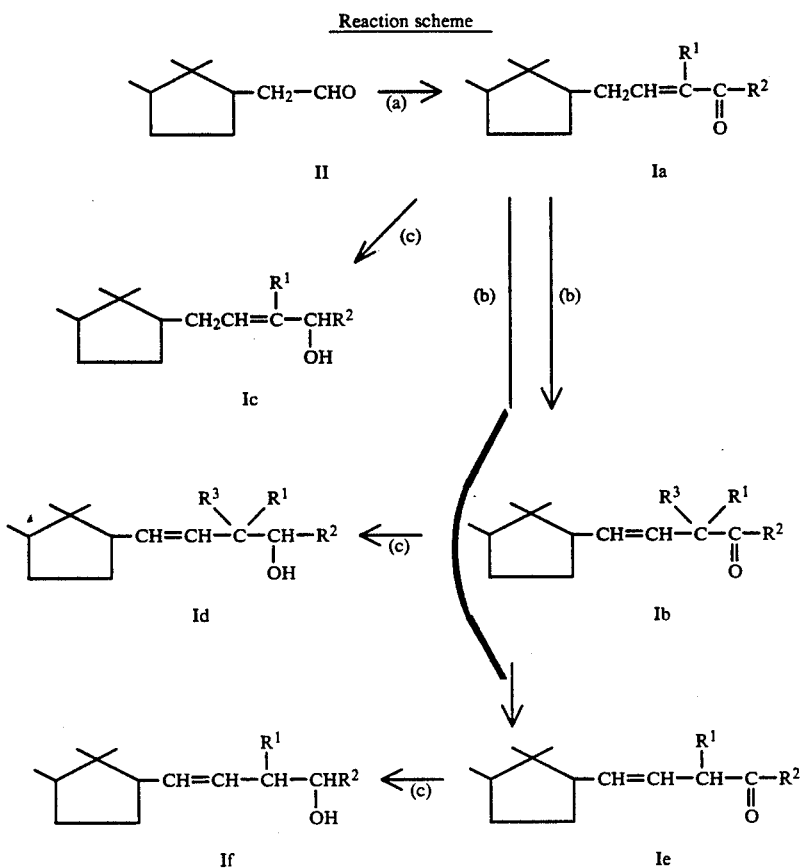

The particular, individual steps involve chemistry similar to that known to one skilled in the art, namely (a) the aldol condensation—under the influence of bases, preferably strong bases, e.g. inorganic or organic bases (b) a deconjugation of Ia, using a strong base, and an optional alkylation using a conventional alkylating agent such as a halide or a sulfate, and optionally, a phase transfer catalyst. In fact, b) involves a deprotonation of Ia, using a strong base, followed by 1) a reprotonation or 2) an alkylation (c) a selective reduction of a carbonyl group in a molecule having C=C bonds, using, e.g. the usual hydrides.

The details of the methods are outlined in the Examples. It is a matter of course that modifications concerning the reagents and reaction conditions are possible. Such are embraced by the claims, since the originality of the access to, e.g. compounds I resides in the selection of the various steps and its linking together.

As pointed out above, it has been found that the novel compounds I possess valuable odorant properties and can accordingly be used as odorants. They are distinguished by very natural notes in the direction of fruity and flowery. Worthy of mentioning is in particular a frequent combination of these notes, this combination of notes being of particular interest because of the resulting powerful notes. They are not only suited in odorant compositions of the flowery type, but also of many other types, especially those suited in the field of the luxury perfumery. They exhibit good substantivity, especially in fabric softeners and detergents.

The olfactory notes of primary interest of I can be characterized as follows: fruity, flowery; woody (in particular sandal) side notes.

On the basis of their olfactory notes the compounds of formula I are especially suitable for modifying and intensifying known compositions. In particular, their extraordinary olfactory strength, which contributes quite generally to the refinement of the compositions, should be emphasized.

The alcohols are generally preferred with the following compounds being in the foreground of the interest:

3,3-dimethyl-5-(2,2,3-trimethyl-cyclopent-1-yl)-pent-4-en-2-ol 3-methyl-5-(2,2,3-trimethyl-cyclopent-1-yl)-pent-3-en-2-ol 3-methyl-5-(2,2,3-trimethyl-cyclopent-1-yl)-pent-4-en-2-ol.

The novel compounds combine with numerous known odorant ingredients of natural or synthetic origin, whereby the range of the natural raw substances can embrace not only readily-volatile, but also moderately-volatile and slightly-volatile components, and that of the synthetics can embrace representatives from practically all classes of substances, as will be evident from the following compilation:

Natural products, such as tree moss absolute, basil oil, citrus fruit oils (such as bergamot oil, mandarin oil, etc.), mastix absolute, myrtle oil, palmarosa oil, patchouli oil, petitgrain oil Paraguay, wormwood oil, alcohols, such as farnesol, geraniol, linalool, nerol, phenylethyl alcohol, rhodinol, cinnamic alcohol, neolinalool Dimetol ® (Givaudan) (2,6-dimethylheptan-2-ol).

aldehydes, such as citral, α-methyl-3,4-methylene-dioxy-hydrocinnamic aldehyde, α-hexyl-cinnamaldehyde, hydroxycitronellal, Lilial ® (Givaudan) (p-tert.butyl- α-methyl-dihydrocinnamaldehyde), methylnonylacetaldehyde, ketones, such as allylionone, α-ionone, β-ionone, Isoraldein ® (Givaudan) (isomethyl-α-ionone), methylionone, Fixolide ® (Givaudan) (1,1,2,4,4,7-hexamethyl-6-acetyl-1,2,3,4-tetrahydronaphthalene). esters, such as allyl phenoxyacetate, benzyl salicylate, cinnamyl propionate, citronellyl acetate, citronellyl ethoxalate (citronellyl).O—CO—CO.OC$_2$H$_5$), decyl acetate, dimethylbenzylcarbinyl acetate, dimethylbenzylcarbinyl butyrate, ethyl acetoacetate, ethyl acetylacetate, hexenyl isobutyrate, linalyl acetate, methyl dihydrojasmonate, styrallyl acetate, vetiveryl acetate, o-tert.butylcyclohexyl acetate etc.

lactones, such as γ-undecalactone, various components often used in perfumery, such as musk ketone, indole, p-menthane-8-thiol-3-one, methyleugenol.

The novel compounds can be used in wide limits which can range in compositions, for example, from about 0.1 (detergents)—about 20% (alcoholic solutions), without these values being, however, limiting values, as the experienced perfumer can also achieve effects with even lower concentrations or can synthesize novel complexes with even higher amounts. The preferred concentrations range between about 1 and about 10%. The compositions manufactured with 1 can be used for all kinds of perfumed consumer goods (eau de cologne, eau de toilette, extracts, lotions, creams, shampoos, soaps, salves, powders, toothpastes, mouth washes, deodorants, detergents, fabric conditioners, tobacco, etc.).

The novel compounds can accordingly be used in the manufacture of compositions and—as the above compilation shows—using a wide range of known odorants or odorant mixtures. In the manufacture of such compositions the known odorants referred to above can be used according to methods known to the perfumer such as e.g. from W. A. Poucher, Perfumes, Cosmetics and Soaps 2, 7th Edition, Chapman and Hall, London, 1974.

ILLUSTRATION OF THE PREFERRED EMBODIMENTS

EXAMPLE 1

2,2,3-Trimethyl-cyclopent-1-yl-acetaldehyde

A three liter autoclave with a stirrer is charged with 830 g of campholenic aldehyde and 56 g of catalyst Pd(5%)/C. Hydrogen is introduced until the pressure reaches 30 bars. The mixture is heated up to 80° C. with stirring for five hours. The calculated amount of hydrogen is now absorbed. The catalyst is separated by filtration and washed with ethanol. The solvent is removed by vacuum evaporation and 815 g of crude saturated aldehyde are obtained (purity: 95%, GC). The vacuum distillation of the crude through a Widmer column gives 763 g of pure product (purity 95%); bp$_{20}$ 85° C.; n$_D^{20}$: 1,4553;

IR: 1730 cm$^{-1}$ $^1$H NMR (400 MHz; CDCl$_3$): 0.54 (3H, s); 0.89 (3H, s); 0.85 (3H, 1 doublet J=7 Hz); 9.78 (1H, fours lines aldehydic proton (1H,m)): δ ppm. No signal in the 5.0-7.0 δ region, indicating no olefinic protons.

EXAMPLE 2

3-Methyl-5-(2,2,3-trimethyl-cyclopent-1-yl)-pent-3-en-2-one

To a stirred solution of 400 g (5.56 moles) of methyl ethyl ketone, 500 ml of methanol, 40 g (0.64 moles) of potassium hydroxyde and 40 g of water are added at room temperature 198 g (1.28 moles) of 2,2,3-trimethylcyclopentyl-1-acetaldehyde (¼ hour). After 3 hours at 30° C., the reaction mass is neutralized by adding H$_2$SO$_4$ (2N), extracted with ether and washed with water. The solvent is removed by rotary evaporation and the oil is fractionally distilled to give 101.6 g of 3-methyl-5-(2,2,3-trimethyl-cyclopent-1-yl)-pent-3-en-2-one (purity: 90%, GC); (38% yield);

bp$_2$: 95° C.; n$_D^{20}$: 1,4826;

IR: 1675 cm$^{-1}$ $^1$H NMR (400 MHz; CDCl$_3$): 0.58 (3H, s); 0.86 (3H, doublet, J=7 Hz); 0.92 (3H, s); 1.77 (3H, 2 lines); 2.3 (3H, s); 6.66 (1H, 1 triplet): δ ppm.

Odour maltol like, cooked fruits, peach, strawberry, woody, fatty.

EXAMPLE 3

3,3-Dimethyl-5-(2,2,3-trimethyl-cyclopent-1-yl)-pent-4-en-2-one

To a rapidly stirred mixture of 400 g of NaOH, 400 g of H$_2$O and 400 ml of toluene are added 8 g of tricaprylmethylammonium chloride (Aliquat 336), then 70 g of 3-methyl-5-(2,2,3-trimethyl-cyclopent-1-yl)-pent-3-en-2-one (0.34 moles) at room temperature. At the end of the addition methyl chloride is injected over ~20 hours. The temperature reaches 30° C. The reaction is monitored by GC. After 20 hours the alkylation is finished and the reaction mass is poured into ice. The resulting mixture is extracted with ether. The organic phase is washed with H$_2$O and the solvents are removed by evaporation. The distillation of the crude product using a Widmer column leads to 38 g of pure ketone (purity: 96%, GC).

bp$_2$: 92° C.; n$_D^{20}$: 1,4706;

IR: 1715 cm$^{-1}$ $^1$H NMR (400 MHz, CDCl$_3$); 0.52 (3H, s); 0.85(s)+0.84 (d, J=7 Hz) 6H; 1.21 (3H, 1s); 1.22 (3H, 1s); 2.12 (3H, 1s); 5.44–5.46 (2H, m): δ ppm.

Odour fruity (exotic fruits, e.g. guava, papaya), fresh, sandalwood.

EXAMPLE 4

3,3-Dimethyl-5-(2,2,3-trimethyl-cyclopent-1-yl)-pent-4-en-2-ol

To a stirred solution of 4.56 g of NaBH$_4$ (0.12 moles) in 250 ml of ethanol is added dropwise 36 g (0.16 moles) of 3,3-dimethyl-5-(2,2,3-trimethyl-cyclopent-1-yl)-pent-4-en-2-one in 100 ml of ethanol (1 hour, 0° C.). The reaction mixture is stirred for 1½ hours at room temperature. (The reduction is monitored by GC). The ethanol is removed by rotary evaporation and the reaction mass is extracted with ether and washed with H$_2$O. After evaporation of the solvent the crude product is vacuum distilled through a Widmer column. The fractional distillation gives 29.5 g of pure alcohol, (purity 99%, GC) which contains mainly the cis isomer.

bp$_4$: 98° C.; n$_D^{20}$: 1,4760;

IR: 3420 cm$^{-1}$ $^1$H NMR (200 MHz; CDCl$_3$); 0.52 (3H, s); 0.86 (s)+0.84 (d,J=7 Hz)=6H; 0.99 (3H, s); 1.01 (3H, s); 1.11 (3H, d); 3.42-3.54 (1H, m); 5.36-5.38 (2H, m) δ ppm.

Odour fruity, floral, sweet, milky, sandalwood.

EXAMPLE 5

3-Methyl-5-(2,2,3-trimethyl-cyclopent-1-yl)-pent-3-en-2-ol

A suspension of 0.9 g (24 mmoles) of LiAlH$_4$ in 30 ml of dry Et$_2$O is added dropwise to a stirred solution of 10 g (48 mmoles) of 3-methyl-5-(2,2,3-trimethyl-cyclopent-1-yl)-pent-3-en-2-one in 30 ml of dried Et$_2$O. The reaction mixture is maintained under argon and refluxed for two hours. It is cooled in ice water and cautiously treated first with ice water, until hydrogen evolution ceases, and then with 10% HCl, whereupon the aluminium hydroxide precipitate dissolves. The material is extracted with ether and the combined organic phases are washed with saturated brine, dried over MgSO$_4$ and distilled. The fractional vacuum distillation gives 6.7 g of the desired alcohol (purity: 95%, GC).

bp$_{0.6}$: 95° C.; n$_D^{20}$: 1,4770;

IR: 3350 cm$^{-1}$ $^1$H NMR (80 MHz; CDCl$_3$): 0.52 (3H, s); 1.21 (3H, 1 doublet); 1.61 (3H, s); 4.16 (1H, 1 quartet); 5.40 (1H, 1 triplet): δ ppm.

Odour milky, fruity, sandalwood.

EXAMPLE 6

2-Methyl-4-(2,2,3-trimethyl-cyclopent-1-yl)-but-2-enal

A mixture of 40 g (0.26 moles) of dihydrocampholenic aldehyde and 30 g (0.52 moles) of freshly distilled propionaldehyde is added drop by drop over ½ hour to a stirred solution of 3 ml of 40% aqueous sodium hydroxide and 120 ml of methanol. The mixture is heated to reflux for 2½ hours, cooled to room temperature and poured into 100 ml of water. The resultant solution is extracted with 250 ml of hexane and the combined hexane extracts are neutralized with a 10% aqueous solution of HCl, then washed with water. The solvent is removed by distillation and the oil fractionally distilled to yield 2-methyl-4-(2,2,3-trimethylcyclopent-1-yl)-but-2-enal (mixture of isomers): 30.1 g (60% yield);

bp$_{0.2\ mmHg}$: 72° C.; n$^{20}$: 1,4843;

IR: 2720 cm$^{-1}$, 1695 cm$^{-1}$, 1650 cm$^{-1}$ $^1$H NMR (200 MHz; CDCl$_3$): 0.58 (3H, s); 0.86 (3H, 1 doublet, J=7 Hz); 0.92 (3H, s); 1.77 (3H, s); 6.53 (1H, 1 triplet); 9.39 (1H, s): δ ppm.

Odour

Celery, sandalwood, orris.

EXAMPLE 7

3-Methyl-5-(2,2,3-trimethyl-cyclopent-1-yl)-pent-4-en-2-one

To a mixture of 100 ml of N,N-dimethylformamide and 13 g (0.18 mole) of powdered potassium butoxide, maintained at 20°-30° C. are added slowly within 1 hour 25 g (0.12 mole) of 3-methyl-5-(2,2,3-trimethyl-cyclopent-1-yl)-pent-3-ene-2-one. The resultant mixture is stirred at ambient temperature for 4 hours (reaction is monitored by GC) and is cooled to 10° C. The reaction mixture is drained out of the reaction flask into a beaker containing 20 ml of glacial acetic acid and 50 ml of ice water which are being stirred by means of a magnetic stirrer. The mixture is stirred for 5-10 minutes and is then transferred to a separatory funnel. This mixture is extracted with three 50 ml portions of toluene. The toluene extracts are combined and washed with three 50 ml portions of 10% sodium bicarbonate solution and one 100 ml portion of saturated sodium chloride solution. The solvent is removed by rotary evaporation and the oil is fractionally distilled to yield 5.2 g of 3-methyl-5-(2,2,3-trimethyl-cyclopent-1-yl)-pent-4-en-2-one (mixtures of isomers).

bp$_{0.1\ mmHg}$: 66° C.; n$^{20}$: 1,4688;

IR: 1750 cm$^{-1}$ $^1$H NMR (400 MHz; CDCl$_3$): 0.5-2.20: very complicated spectrum; 3.1-3.23 ($_1$H at α of carbonyl, m); 5.3-5.4 ($_1$H olefinic, m); 5.48-5.56 ($_1$H olefinic m): δ ppm.

Odour fruity, woody, leather.

EXAMPLE 8

2-Methyl-4-(2,2,3-trimethyl-cyclopent-1-yl)-but-2-en-1-ol

To a stirred suspension of 1.5 g (0.04 mole) of lithium aluminium hydride and 75 ml of dried diethyl ether are added over ½ hour 15 g (0.08 moles) of 2-methyl-4-(2,2,3-trimethylcyclopent-1-yl)-but-2-enal. The mixture is heated under argon to reflux for 2 hours. It is cooled with ice water and, with caution, treated first with water until hydrogen no longer evolves and then with HCl 5%, whereupon the aluminium hydroxide precipitate dissolves. The material is extracted with ether and the combined organic phases are washed with saturated common salt; it is then dried over MgSO$_4$ and distilled. A fractional vacuum distillation leads to 8.3 g of 2-methyl-4-(2,2,3-trimethyl-cyclopent-1-yl)-but-2-en-1-ol (mixture of isomers) (55% yield);

bp$_{0.3\ mmHg}$: 79° C.; n$^{20}$: 1,4812;

IR: 3330 cm$^{-1}$ $^1$H NMR (200 MHz; CDCl$_3$): 0.56 (3H, s); 0.84 (3H, d, J=8 Hz); 0.88 (3H, s); 1.68 (3H, s); 4.0 (2H, broad line); 5.42 (1H, m).

Odour weak, mild, creamy, milky, fat, orris-like, reminiscent of sandalwood.

EXAMPLE 9

3-Methyl-5-(2,2,3-trimethyl-cyclopent-1-yl)-pent-4-en-2-ol

To a stirred solution of 0.58 g of NaBH$_4$ (18 mmoles) in 50 ml of ethanol cooled to 0° C. are added drop by drop within one hour 5 g (24 mmoles) of 3-methyl-5-(2,2,3-trimethyl-cyclopent-1-yl)-pent-4-en-2-one. The reaction mixture is stirred for 90 minutes at room temperature. The ethanol is removed by rotary evaporation and the reaction mass is extracted with ether and washed with water. After evaporation of the solvent the crude product is vacuum distilled, to yield 3-methyl-5-(2,2,3-trimethyl-cyclopent-1-yl)-pent-4-en-2-ol: 4.4 g (mixture of isomers)

bp$_{0.5\ mmHg}$: 75° C.; n$^{20}$: 1,4740;

IR: 3370 cm$^{-1}$ $^1$H NMR (200 MHz; CDCl$_3$): 0.5-2.30 (23H, very complicated spectrum); 3.41-3.70 (1H, m); 5.19-5.57 (2H olefinic, m): δ ppm.

Odour woody (sandalwood), fruity, lactonic.

EXAMPLE 10

| Odorant compositions a) Odorant composition (e.g. for soaps) (hesperidin, flowery, green) | | |
|---|---|---|
| | parts per weight | |
| Benzyl acetate | 100.00 | — |
| Geranyl acetate | 100.00 | — |
| p-tert.Butyl cyclohexyl acetate | 100.00 | — |
| Verdyl acetate | 20.00 | — |
| Phenylethyl alcohol | 150.00 | — |
| Hexyl cinnamic aldehyde | 100.00 | — |
| Bergamotte essence | 200.00 | — |
| Cyclohexyl allyl propionate | 1.00 | — |
| Dimetol ® (Givaudan) (2,6-dimethylheptan-2-ol) | 20.00 | — |
| Dipropylene glycol | 10.00 | 30.00 |
| Gardenol ™ (Givaudan) (methyl phenyl carbinyl acetate) | 2.00 | — |
| Isoeugenol | 2.00 | — |
| Linalool | 50.00 | — |
| Geranium oxyde (rose oxide) 10%/DIP | 5.00 | — |
| Petitgrain essence | 20.00 | — |
| Benzyl salicylate | 100.00 | — |
| Compound of Example 4 | 20.00 | |
| | 1000.00 | 1000.00 |

The addition of the novel I ($R^1=R^2=R^3=CH_3$) brings about volume and richness, two aspects which are appreciated not only in the top notes but throughout the evaporation of the resulting perfume.

| b) Odorant composition (1% in shower gels) (flowery, fruity, hesperidin) | | |
|---|---|---|
| | parts per weight | |
| Benzyl acetate | 80.00 | — |
| Geranyl acetate | 150.00 | — |
| Linalyl acetate | 200.00 | — |
| p-t-Butyl cyclohexyl acetate | 100.00 | — |
| o-tert.Butyl cyclohexyl acetate | 80.00 | — |
| Phenyl propyl alcohol | 100.00 | — |
| Dipropylene glycol | 30.00 | 50.00 |
| Eugenol | 10.00 | — |
| Isoraldeine ® 70 (Givaudan) (isomethyl-α-ionone) | 50.00 | — |
| Lemarome ® A (Givaudan) (neral + citral) | 30.00 | — |
| Hexyl salicylate | 50.00 | — |
| Tetrahydrolinalool | 100.00 | — |
| Compound of Example 4 | 20.00 | |
| | 1000.00 | 1000.00 |

By the addition of the novel I ($R^1=R^2=R^3=CH_3$) the flowery notes are amplified and at the same time favorably modified with a touch of noblesse and elegance.

| c) Odorant composition (e.g. 6% in eau de toilette for men) (woody, amber, tobacco) | | |
|---|---|---|
| | parts per weight | |
| Methyl dihydrojasmonate | 180.00 | — |
| Patchouli essence | 170.00 | — |
| Linalyl acetate | 120.00 | — |
| Cedryl methyl ether | 110.00 | — |
| Methyl cedryl cetone | 85.00 | — |
| Cyclohexal | 72.00 | — |
| Lavandin essence | 52.00 | — |
| Bergamotte essence | 39.00 | — |
| Tangerin essence | 26.00 | — |
| Citronellol | 20.00 | — |
| Coumarin pure crist. | 20.00 | — |
| Dipropylene glycol | — | 13.00 |
| Butyl hydroxy toluene | 5.00 | — |

-continued

| c) Odorant composition (e.g. 6% in eau de toilette for men) (woody, amber, tobacco) | | |
|---|---|---|
| | parts per weight | |
| Linalool | 13.00 | — |
| Cedarwood essence | 13.00 | — |
| Fixambrene ™ (Givaudan) 10%/DIP (3A,6,6,9a-tetramethyl-dodecahydro-naphtho(2,1β)furan) | 7.00 | — |
| Vanillin | 6.00 | — |
| Civet absolue 10%/DIP | 5.00 | — |
| Ylang Ylang essence | 7.00 | — |
| Vetiver essence Bourbon | 7.00 | — |
| Geranium essence | 6.00 | — |
| Givescone ® (Givaudan) 10%/DIP ((2-ethyl-6,6-dimethyl-2-cyclohexane-1-carboxylic acid ethyl ester)) | 5.00 | — |
| Castoreum odoresine (Castoreum resinoid)10%/DIP | 5.00 | — |
| Fixolide ® (Givaudan) 1,1,2,4,4,7-hexamethyl-6-acetyl-1,2,3,4-tetrahydronaphthalene) | 4.00 | — |
| Lemon essence conc. | 5.00 | — |
| Mandarine aldehyde DA 10%/DIP (dodec-2-en-1-al) | 5.00 | — |
| Compound of Example 4 | 13.00 | |
| | 1000.00 | 1000.00 |

The addition of the novel I ($R^1=R^2=R^3=CH_3$) links the flowery notes (Jasmin, Rose, Ylang) with the woody notes (e.g. Patchouli) and the animalic and amber-like notes to yield a round, well-balanced and rich eau de toilette.

I claim:

1. A compound of the formula:

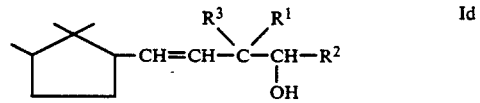
                                              Id wherein each of $R^1$, $R^2$ and $R^3$ is alkyl of one to four carbon atoms.

2. The compound according to claim 1 which is 3,3-dimethyl-5-(2,2,3-trimethyl-cyclopent-1-yl)-pent-4-en-2-ol.

3. An odorant composition having a compound the formula:

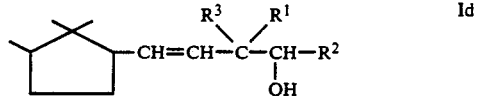
                                              Id wherein each of $R^1$, $R^2$ and $R^3$ is alkyl of one to four carbon atoms, and a carrier material.

4. An odorant composition according to claim 3 wherein the compound is 3,3-dimethyl-5-(2,2,3-trimethyl-cyclopent-1-yl)-pent-4-en-2-ol.

5. A method for improving the odor of an odorant composition which comprises adding thereto an olfactorily effective amount of a compound of the formula:

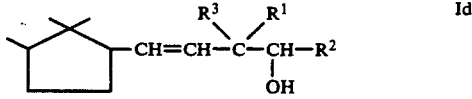
                                              Id wherein each of $R^1$, $R^2$ and $R^3$ is alkyl of one to four carbon atoms.

6. A method according to claim 5 wherein the compound to be added is 3,3-dimethyl-5-(2,2,3-trimethyl-cyclopent-1-yl)-pent-4-en-2-ol.

* * * * *